United States Patent [19]

Ishiwatari

[11] Patent Number: 4,680,102

[45] Date of Patent: Jul. 14, 1987

[54] ELECTROPHORETIC APPARATUS

[75] Inventor: Shiro Ishiwatari, Hino, Japan

[73] Assignee: Olympus Optical Co., Ltd., Japan

[21] Appl. No.: 800,683

[22] Filed: Nov. 22, 1985

[30] Foreign Application Priority Data

Nov. 28, 1984 [JP] Japan ................. 59-251172

[51] Int. Cl.⁴ ............... C25D 13/00; G01N 21/00
[52] U.S. Cl. ................. 204/299 R; 204/182.9; 204/182.8
[58] Field of Search ............ 204/299 R, 182.8, 182.7

[56]       References Cited
        U.S. PATENT DOCUMENTS 3,616,457  10/1971  Hjerten et al. ........... 204/182.8 X
3,909,380  9/1975   Day et al. .................. 204/299 R X
4,234,400  11/1980  Kaplan et al. ............... 204/182.8
4,310,407  1/1982   Kaneko et al. ............. 204/182.7 X Primary Examiner—Donald R. Valentine
Attorney, Agent, or Firm—Parkhurst & Oliff

[57]             ABSTRACT

An electrophoretic apparatus for effecting an electrophoresis by conducting an electrophoretic current through a substrate on which a sample has been applied, while the substrate is maintained in a wetted condition with a buffer solution includes a device for detecting a variation of an expansion length of fraction images and a device for controlling a condition of the electrophoretic operation. Further a condition of the buffer solution is monitored and the buffer solution is fully or partially replaced by a fresh buffer solution.

10 Claims, 8 Drawing Figures

ELECTROPHORETIC APPARATUS

BACKGROUND OF THE INVENTION

1. Field of the Invention

The present invention generally relates to an electrophoretic technique, and more particularly to an electrophoretic apparatus for forming an electrophoretic image by placing a substrate on which a sample has been applied in an electrophoretic vessel containing a buffer solution and conducting an electric current through the substrate.

2. Related Art Statement

Heretofore, there has been practiced an automatic chemical analyzer utilizing an electrophoresis. Such an analyzer has been used for analyzing biological high molecular substances such as various kinds of proteins contained in a serum sample. In the electrophoretic apparatus, after a sample serum has been applied on a substrate made of, for instance, cellulose acetate film wetted with a buffer solution, an electric current is flowed through the substrate while the substrate remains wet in an electrophoretic chamber containing the buffer solution to effect the electrophoresis. Then electrophoretic images of various kinds of components contained in the sample are formed on the substrate separately from each other. The electrophoretic images are visualized and the visible images are optically scanned by means of a densitometer and fraction images are operationally processed to effect a quantitative analysis for respective components in the sample.

In the electrophoretic apparatus mentioned above, the buffer solution contained in the electrophoretic chamber for keeping the substrate in the wetted condition is deteriorated due to fatigue. If the degree of fatigue of the buffer solution changes, the electrophoretic operation is varied and it is no longer possible to form the electrophoretic images precisely. Further the temperature of the buffer solution might be increased due to the supply of electric current and pH value and concetration of the buffer solution might be also varied. Due to these variations the electrophoretic images could not be obtained accurately and therefore there might be produced an analysis error. Under the above circumstances, in order to increase the analysis accuracy it is very important to detect the condition of the buffer solution in the electrophoretic chamber.

In the known electrophoretic apparatus, an operator judges the condition of the buffer solution by visually inspecting an expansion length and disturbances of the electrophoretic images formed on the substrate. Therefore, it is difficult to detect the condition of the buffer solution precisely and there is sometimes introduced a serious analysis error.

SUMMARY OF THE INVENTION

The present invention has for its object to provide an electrophoretic apparatus which can remove the drawback mentioned above and can detect the condition of the buffer solution accurately and automatically.

It is still another object of the invention to provide an electrophoretic apparatus in which the condition of the buffer solution can be controlled precisely so that the electrophoretic analysis can be performed at a high precision.

According to the invention, an electrophoretic apparatus for effecting an electrophoresis by placing a substrate on which a sample has been applied in an electrophoretic chamber containing a buffer solution and by conducting an electric current through the substrate, comprises
means for detecting a variation of an expansion length of electrophoretic images formed on the substrate.

In a preferred embodiment of the electrophoretic apparatus according to the invention there is further provided means for controlling a condition of the electrophoretic operation in accordance with the detected variation of the expansion length.

DESCRIPTION OF THE PREFERRED EMBODIMENTS

Figure 1:
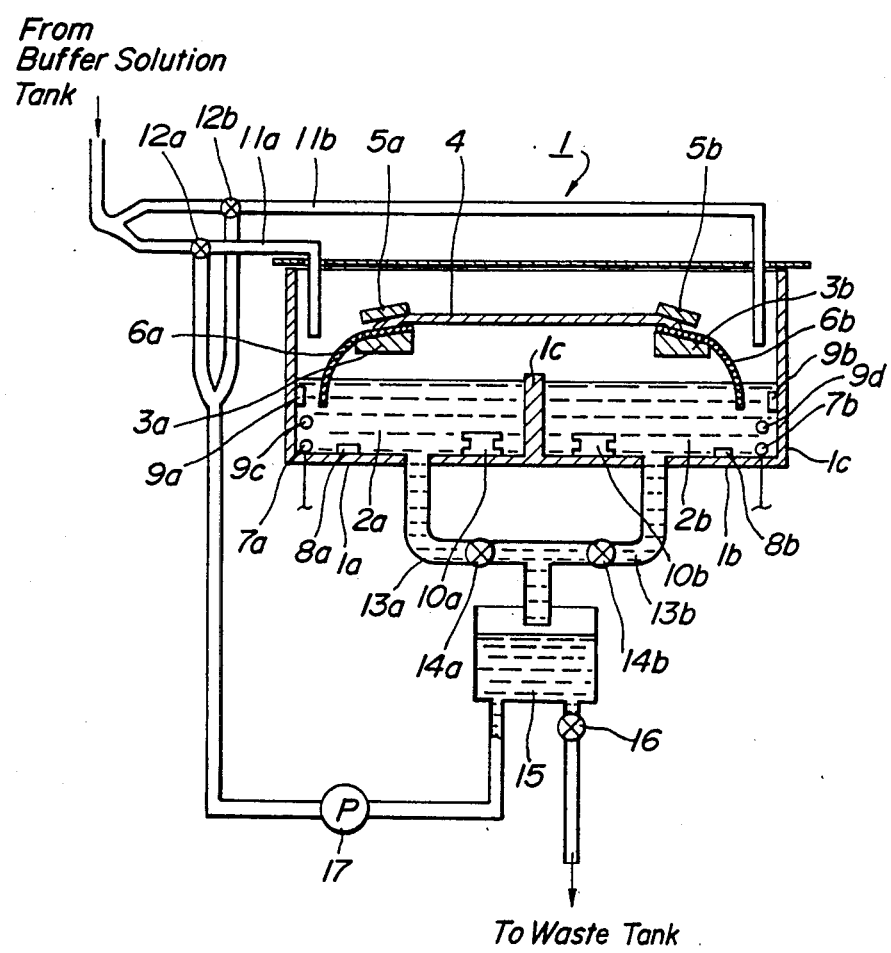
FIG. 1 is a schematic cross sectional view showing an embodiment of the electrophoretic chamber of the electrophoretic apparatus according to the invention.

FIG. 1 is a schematic cross sectional view showing an embodiment of an electrophoretic chamber of the electrophoretic apparatus according to the invention. The electrophoretic chamber 1 is generally of a double vessel construction having two vessels 1a and 1b divided by a partition wall 1c. In these vessels are contained buffer solutions 2a and 2b which are not mixed with each other. Above the buffer solutions 2a and 2b in the vessels 1b and 1c there are arranged supporting plates 3a and 3b on which a substrate 4 is placed, and pushing plates 5a and 5b are arranged movably with respect to the supporting plates 3a and 3b. In this manner, the substrate 4 is clamped along its side edges between the supporting and pushing plates 3a, 3b and 5a, 5b. It should be noted a sample to be analyzed has been applied on the substrate 4. Further, one side edges of filtering papers 6a and 6b are clamped between the supporting plates 3a, 3b and the substrate 4, and the other side edges of the filtering papers are immersed in the buffer solutions 2a, 2b. In this manner, the substrate 4 is effectively wetted with the buffer solutions 2a, 2b by means of the filtering papers 6a and 6b having the capilary phenomenon. In the vessles 1a and 1b there are arranged electrodes 7a and 7b for conducting an electric current through the substrate 4, these electrodes being connectable to a power supply source not shown. In the vessels 1a and 1b there are further provided pH sensors 8a and 8b for detecting pH values of the buffer solutions 2a and 2b, respectively, temperature sensors 9a and 9b for measuring temperatures of the buffer solutions 2a and 2b, respectively, and concentration sensors 9c and 9d for detecting concentrations of the buffer solutions 2a and 2b, respectively. In this manner, accordng to the invention the pH values, temperatures and concentrations of the buffer solutions 2a and 2b are detected and detected signals are supplied to a central control device as will be explained later. Moreover, heat exchanging elements 10a and 10b are arranged in the chambers 1a and 1b so as to heat or cool the buffer solutions 2a and 2b, respectively. There are further provided buffer solution supply tubes 11a and 11b which are connected via respective three-way valves 12a and 12b to a buffer solution tank (not shown). By means of this a fresh buffer solution may be selectively introduced into the electrophoretic vessels 1a and 1b. In bottoms of the vessels 1a and 1b are connected discharge tubes 13a and 13b which are connected to a mixing tank 15 via valves 14a and 14b. In the mixing tank 15, the buffer solutions discharged from the vessels 1a and 1b are mixed and then a mixed buffer solution is recharged into the vessels 1a and 1b by means of a pump 17, the valves 12a and 12b and tubes 11a and 11b, respectively. In case of discharging a fatigued buffer solution, the buffer solution in the mixing tank 15 is flowed into a waste tank via a valve 16.

After the electrophoretic process has been completed, electrophoretic images formed on the substrate 4 are visualized by subjecting the substrate to the coloring, decoloring and transparentizing processes and then a densitogram pattern of the electrophoretic images is photoelectrically detected by means of a densitometer.

Figure 2A:
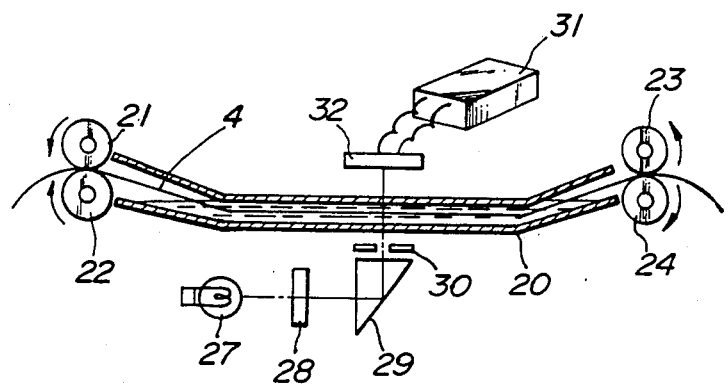
FIGS. 2A and 2B are schemtic cross sectional and plan views, respectively illustrating an embodiment of a densitometer of an electrophoretic apparatus according to the invention.
Figure 2B:
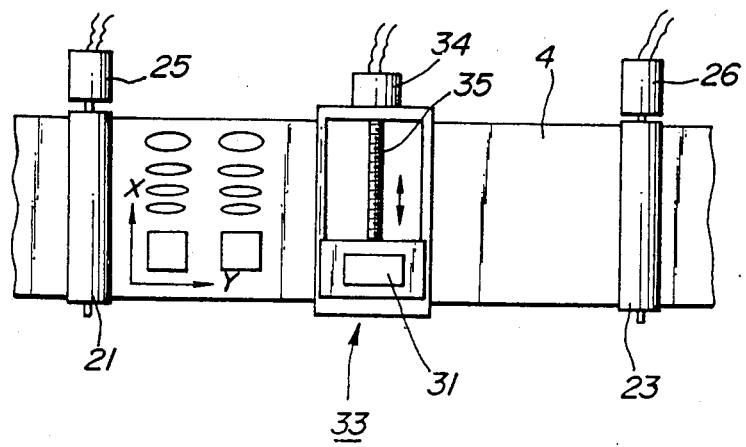

FIGS. 2A and 2B show an embodiment of the densitometer of the electrophoretic apparatus according to the invention. FIG. 2A is a schematic cross sectional view and FIG. 2B is a schematic plan view. The densitometer comprises a transparent vessel 20 in which a transparentizing liquid such as decalin is contained. A pair of feed rollers 21 and 22 are arranged at an entrance of the vessel 20 and a pair of feed rollers 23 and 24 are arranged at an exit of the vessel. The feed rollers 21 and 23 are coupled with driving motors 25 and 26, respectively as illustrated in FIG. 2B.

The substrate 4 having the visualized electrophoretic images formed thereon is introduced into the vessel 20 by means of the rollers 21 and 22. When the substrate 4 is immersed into the transparentizing liquid, the substrate is made transparent and the electrophoretic images are indexed to an optically measuring position provided at a bottom of the transparent vessel 20. At the measuring position, a light source device comprising light source 27, filter 28, rectangular prism 29 and slit 30, and a photodetector 32 connected to a signal processing unit 31 are provided under and above the vessel 20, respectively. The light source device and photodetector 32 are coupled with a scanning device 33.

The scanning device 33 comprises step motor 34 and driving shaft 35 in the form of a lead screw coupled with the step motor 34. By driving the step motor 34 step by step, the scanning device 33 and thus the light source device 27 to 30 and photodetector 32 are moved in X direction in which the electrophoresis has occurred to measure a densitogram pattern of the fraction images (electrophoretic images). At the same time, the substrate 4 is moved in the Y direction by means of the rollers 21 to 24 so that densitogram patterns of samples applied on the substrate are detected successively.

Figure 3A:
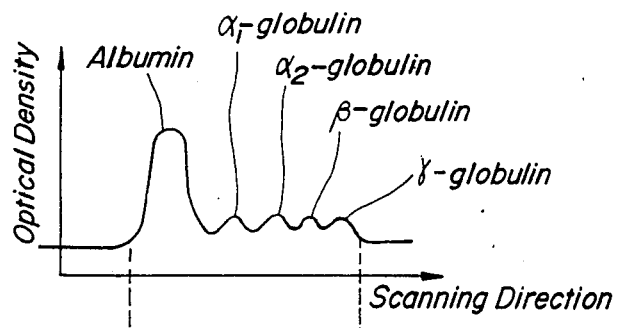
FIGS. 3A to 3D are signal waveforms for explaining the operation of the expansion length detecting means according to the invention.
Figure 3B:
Figure 3C:
Figure 3D:
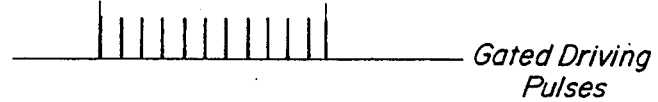

FIG. 3A shows a pattern of fraction images, FIG. 3B a bivalent signal of the pattern obtained by quantitizing the fraction image signal, FIG. 3C driving pulses supplied to the step motor 34 and FIG. 3D illustrates pulses denoting an expansion length of the fraction images detected by counting the member of driving pulses gated by the bivalent signal. In the present embodiment, various proteins contained in a serum sample are to be tested quantitatively. In such an analysis an electrophoretic image of albumin is formed as a first fraction image and electrophoretic images of $\alpha_1$-globulin, $\alpha_2$-globulin, $\beta$-globulin and $\gamma$-globulin are successively formed in the X direction. Upon investigating these fraction images, the following facts have been derived.

(1) As long as the buffer solution is not fatigued, the expansion length of the fraction images measured in the X direction is substantially same for various samples. But when the buffer solution is fatigued, the expansion length becomes short in accordance with the degree of fatigue.

(2) When the temperature, concentration and pH value of the buffer solution are varied, the expansion length of the fraction images is varied accordingly.

From the above facts, the inventor has confirmed that the degree of deterioration of the buffer solution can be detected automatically and accurately by measuring the expansion length of fraction images, and that the precision of measurement of the condition of the buffer solution can be further increased by measuring the temperature, pH value and concentration of the buffer solution. For instance, if the temperature, and pH value of the buffer solution are correct, but the expansion length of fraction images is shortened, one can judge that the buffer solution is fatigued. In such a case, the condition of the electrophoresis is adjusted so that the expansion length of fraction images is prolonged by increasing the electrophoretic current and/or voltage or by prolonging an electrophoretic time period. Further if the temperature of the buffer solution is higher or lower than a standard value and the expansion length is beyond an acceptable range, the buffer solution is cooled or heated by the heat exchanging element. Moreover, if the pH value and/or concentration of the buffer solution are beyond acceptable ranges and the expansion length is deviated from the standard value, the buffer solution is replaced fully or partially by a fresh buffer solution.

According to the present embodiment, the expansion length of fraction images of respective sample is detected and the expansion length thus detected is compared with a standard expansion length which is obtained when the buffer solution is not fatigued. In this manner the condition of the buffer solution is detected automatically. The expansion length of fraction images can be easily detected in accordance with the relation between the number of pulses applied to the step motor 34 for driving the scanning device 33 and the optical concentration of the fraction images. Therefore, by suitably combining the condition of the buffer solution detected from the expansion length and the temperature, concentration and pH value of the buffer solution measured separately, it is possible to confirm accurately the condition of the buffer solution and to known or analyze causes of variation, and therefore the electrophoretic analysis can always be effected optimally.

Figure 4:
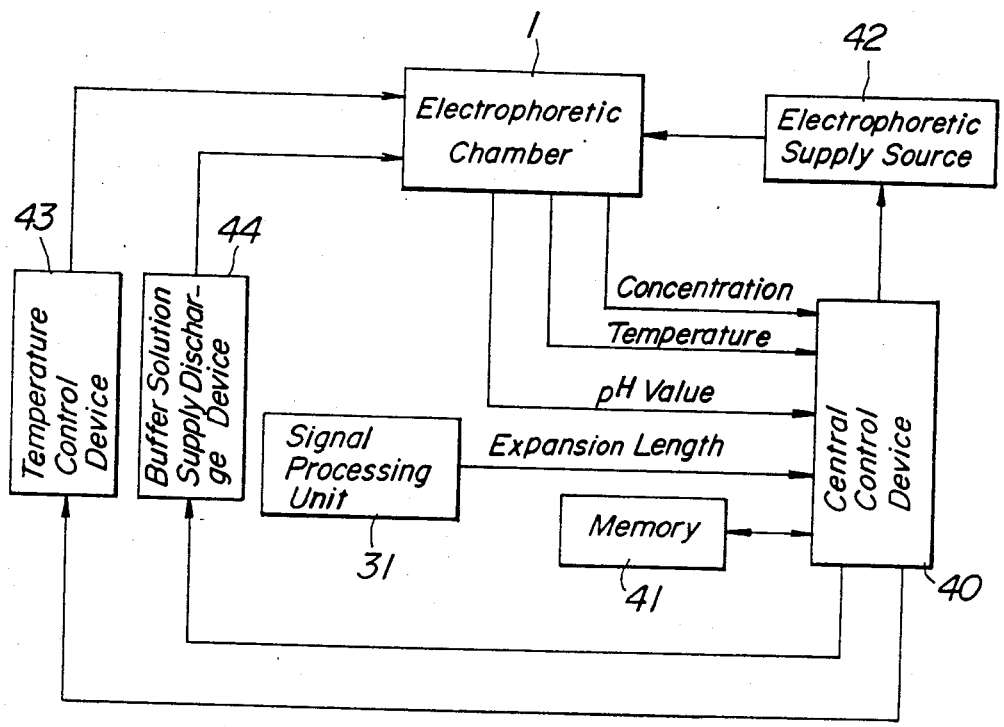
FIG. 4 is a block diagram showing an embodiment of a control unit of the electrophoretic apparatus according to the invention.

FIG. 4 is a block diagram showing an embodiment of a control unit of the electrophoretic apparatus according to the invention. The pH sensors 8a, 8b, temperature sensors 9a, 9b and concentration sensors 9c, 9d provided in the electrophoretic chamber 1 are connected to a central control device 40 so that pH values, temperatures and concentrations of the buffer solutions 2a, 2b contained in the vessels 1a and 1b are entered into the central control device 40. Further the signal processing unit 31 of the densitometer is connected to the central control device 40 so that the detected expansion length of fraction images of respective sample is supplied to the central control device 40. To the central control device 40 is further connected a memory 41 in which there are previously stored standard expansion length, standard pH value, standard temperature, standard concentration and relations between these variables and conditions of the buffer solution. In the central control device 40, the detected expansion length is compared with the standard expansion length to confirm the condition of the buffer solution and further the central control device 40 generates instructions necessary for effecting the correct analysis by considering also the temperature, pH values and concentration of the buffer solution. For instance, when the detected expansion length is shorter than the standard expansion length, the central control device 40 instructs an electrophoretic power supply source 42 to increase electrophoretic voltage and/or current or to prolong a power supply time period. Contrary to this, when the detected expansion length is longer than the standard expansion length, the electrophoretic voltage and/or current or power supply time period is decreased accordingly. When the detected temperature of the buffer solution is deviated from the standard temperature, the central control device 40 sends instructs to a buffer solution temperature control device 43 so that the heat exchange elements 10a and 10b provided in the electrophoretic chamber 1 heat or cool the buffer solutions 2a and 2b, respectively.

Further, when the detected pH values of the buffer solutions 2a and 2b are deviated from the standard pH value, the central control device 40 supplies command to a buffer solution supply and discharge device 44 so that the buffer solutions 2a and 2b are replaced by fresh buffer solutions.

When the detected concentrations of the buffer solutions 2a and 2b are deviated from the standard concentration, the central control device 40 instructs the buffer solution supply and discharge device 44 to replace the old buffer solutions by fresh ones.

It should be noted that the buffer solution may be partially replaced by fresh one in accordance with the degree of deviation of the detected pH values and/or concentrations from the standard values.

Futher, if the temperatures, pH values and/or concentrations of the buffer solutions 2a and 2b contained in the electrophoretic vessels 1a and 1b are different from each other, the central control device 40 sends instruction to the buffer solution supply and discharge device 44 to mix the buffer solutions with each other.

It should be further noted that the standard values may have given ranges. For instance, the standard tempeature may be set to 37° C.±0.1° C. In such a case, when the detected temperature is beyond the predetermined range, the above operation is performed.

As explained above, according to the invention, the condition of the buffer solution can be detected precisely be totally considering the detected expansion length of franction images and the information such as temperature, pH value and concentration of the buffer solution, and thus the electrophoretic analysis can be performed accurately alway under the optimum condition.

What is claimed is:

1. An electrophoretic apparatus for effecting electrophoresis comprising:
    means for wetting a substrate made of cellulose acetate with a buffer solution;
    means for applying a sample on the substrate;
    means for placing the substrate in an electrophoretic chamber containing a buffer solution;
    means for conducting an electric current through the substrate to form an electrophoretic image on the substrate;
    means for dying and decoloring the substrate to make said electrophoretic image visible;
    means for photometering the visable electrophoretic image;
    means for storing a standard expansion length of a standard electrophoretic image;
    means for measuring an expansion length of the electrophoretic image of the sample;
    means for comparing the expansion length of the electrophoretic image of the sample with the standard expansion length of the standard electrophoretic image to derive a variation in the expansion length of the electrophoretic image of the sample; and
    means for adjusting electrophoretic current, electrophoretic voltage or electrophoretic time, in accordance with said variation in the expansion length of the electrophoretic image.

2. An apparatus according to claim 1, wherein said means for adjusting comprises means for adjusting an amplitude of an electrophoretic current passing through the substrate.

3. An apparatus according to claim 1, wherein said means for adjusting comprises means for adjusting an amplitude of an electrophoretic voltage applied to the substrate.

4. An apparatus according to claim 1, wherein said means for adjusting comprises means for adjusting a time period of the eectrophoretic operation.

5. An electrophoretic apparatus for effecting electrophoresis comprising:
    means for wetting a substrate made of cellulose acetate with a buffer solution;
    means for applying a sample on the substrate;
    means for placing the substrate in an electrophoretic chamber containing a buffer solution;
    means for conducting an electric current through the substrate to form an electrophoretic image on the substrate;
    means for dying and decoloring the substrate to make said electrophoretic image visible;
    means for photometering the visible electrophoretic image;
    means for storing a standard expansion length of a standard electrophoretic image;
    means for measuring an expansion length of the electrophoretic image of the sample;
    means for comparing the expansion length of the electrophoretic image of the sample with the standard expansion length of the standard electrophoretic image to derive a variation in the expansion length of the electrophoretic image of the sample;
    means for detecting at least one electrophoretic condition including temperature, pH value and concentration of the buffer solution contained in the electrophoretic chamber; and
    means for adjusting said at least one electrophoretic condition in accordance with said variation in the expansion length of the electrophoretic image and said at least one detected electrophoretic condition.

6. An apparatus according to claim 5, wherein said means for detection comprises a temperature sensor for detecting a temperature of the buffer solution.

7. An apparatus according to claim 5, wherein said means for detecting comprises a pH sensor for detecting a pH value of the buffer solution.

8. An apparatus according to claim 5, wherein said means for detecting comprises a concentration sensor for detecting a concentration of the buffer solution.

9. An apparatus according to claim 5, wherein said means for adjusting comprises a heat exchanging means for heating and cooling the buffer solution.

10. An apparatus according to claim 5, wherein said means for adjusting comprises means for replacing at least partially the buffer solution by a fresh buffer solution.

* * * * *